United States Patent
Magalhães Mendes et al.

(10) Patent No.: US 8,617,061 B2
(45) Date of Patent: Dec. 31, 2013

(54) DEVICE FOR MEASURING AND ANALYSING THE COLOUR OF THE OUTER EAR AND EAR CANAL

(75) Inventors: Joaquim Gabriel Magalhães Mendes, Oporto (PT); Jorge Manuel Matos Reis, Azurara-Vila do Conde (PT); João Manuel Ribeiro Da Silva Tavares, Oporto (PT); Georgeta Maria Costa Alves De Oliveira, Matosinhos (PT); José Jesus Soeira, Oporto (PT)

(73) Assignee: Universidade do Porto, Oporto (PT)

( * ) Notice: Subject to any disclaimer, the term of this patent is extended or adjusted under 35 U.S.C. 154(b) by 120 days.

(21) Appl. No.: 13/054,217

(22) PCT Filed: Jul. 13, 2009

(86) PCT No.: PCT/PT2009/000041
§ 371 (c)(1),
(2), (4) Date: Feb. 18, 2011

(87) PCT Pub. No.: WO2010/008310
PCT Pub. Date: Jan. 21, 2010

(65) Prior Publication Data
US 2011/0152621 A1    Jun. 23, 2011

(30) Foreign Application Priority Data
Jul. 14, 2008 (PT) .......................... 104131

(51) Int. Cl.
*A61B 1/227* (2006.01)
(52) U.S. Cl.
USPC ........................................ 600/200
(58) Field of Classification Search
USPC ......... 600/310, 342, 476–478, 182, 184, 199, 600/200
See application file for complete search history.

(56) References Cited

U.S. PATENT DOCUMENTS
2009/0030295 A1    1/2009   Shioi

FOREIGN PATENT DOCUMENTS
WO    WO 01/35817     5/2001
WO    WO 02/091914    11/2002
WO    WO 2007/105596  9/2007

OTHER PUBLICATIONS
International Search Report for International Application No. PCT/PT2009/000041 dated Apr. 6, 2010.

*Primary Examiner* — Pedro Philogene
*Assistant Examiner* — David Comstock
(74) *Attorney, Agent, or Firm* — Pearl Cohen Zedek Latzer Baratz LLP

(57) ABSTRACT

The present application concerns a device for measurement and analysis of the middle ear and ear channel color for the diagnosis of ear infections. The device is composed of a otoscope (1), including two optical fibers (2a and 2b): one for ear illumination and another returning the reflected light. The electronic unit (3) can change linearly the power of emitted light, as well as, its color. The received light is also independently measured, enabling the determination of changes on color and texture associated with the ear inflammations. Command buttons in the otoscope handler (4) enable the user to save the values of the three color components. The combined value of the components is shown in the digital display (5) of the electronic unit, as well as, by a set of LEDs (6) green, yellow and red that gives a diagnosis in a simple and immediate way. The otoscope allows, simultaneously, directly ear view through a magnifying glass (7) applied in the head of the otoscope, with a standard white light. This device is also useful in food industry.

11 Claims, 3 Drawing Sheets

DEVICE FOR MEASURING AND ANALYSING THE COLOUR OF THE OUTER EAR AND EAR CANAL

TECHNICAL DOMAIN

The device object of this invention can be used in applications where it is useful to have evaluation of colour, particularly in human medicine areas (in particular in the support for ear inflammation diagnosis—otites), veterinarian and food industry. This device allows thus automatic patient middle ear colour measurement and intends to be an equipment to help health professionals in the diagnosis of ear infections.

STATE OF THE ART

Otoscopes are generically devices to aid otitis ear diagnosis. Otitis is ear inflammation that may cause an increase of temperature, accompanied by a change of colour and texture of the tympanum. For this purpose, otoscopes offer local lighting of the ear, usually of white colour, to allow users to view the interior of the ear and to perform the subsequent diagnosis, usually done by a doctor, in a subjective way.

There are several publications that refer otoscopes for direct patient observation.

U.S. Pat. No. 5,345,926 presents a manual otoscope for patient direct observation, with a side white light to assist the expert viewing inside the ear.

Other otoscopes, like the one cited on patent WO03/075761A2 allows the insertion of several sensors, such as infrared temperature sensor for localized temperature measurement, based on the fact that in general the infection will increases the skin temperature.

The audio capability may also be available, as shown in patent WO 2007/039843A2, to listen to music recorded in flash memory to help the patient to relax and to facilitate the examination; specially useful for children diagnosis.

The video is also present in several otoscopes, on the device revealed in the patent US2005/0171399A1, a small camera is docked in the otoscope to show the interior of the ear. Occasionally, these cameras may be prepared to be linked to a computer through a USB connection and to enable image recording.

The analysis of the acoustic echoes waves enables the evaluation without contact of stiffness and texture of the surface, particularly useful in detecting the presence of liquid behind tympanum as revealed by U.S. Pat. No. 6,093,150.

The connection of a pneumatic balloon to the head of the otoscope, or directly at the speculum, allows contactless forced vibration of the tympanum and this way the assessment of its flexibility and of presence of liquids. An example of this technique is described in U.S. Pat. No. 5,873,819.

In the patent WO 2005/011484 is revealed an otoscope with a system for internal lens motion capable of focusing more effectively the ear channel.

None of the otoscopes available on the market, neither revealed in previous patents, incorporates any device for automatic colour measurement.

INVENTION SUMMARY

The device is essentially composed of: a standard otoscope, modified to include two optical fibers, one that illuminates the ear and another that returns the reflected light; and an electronic unit that can change linearly the power of emitted light, as well as, its colour (by combining green, blue and red intensities). The received light is also measured separately in the same three components, allowing the determination of changes in colour or texture, normally associated with ear inflammations. Command buttons placed on the otoscope handler allow the user to save the values of the three colour components. The combined value of components is shown in the digital display of the electronic unit, as well as, by a set of LEDs of green, yellow and red colours, which provide a simple and immediate diagnosis. It allows, simultaneously, the ear direct observation through a lens applied on otoscope head and a standard white light illumination.

The device disclosed in this invention is based on a polychromatic light emitter, resulting from the combination of the RGB components (red, green, blue) and on the measurement of the corresponding reflected light from the interior surface of the ear using RGB colour sensors (red, green, blue). However, the otoscope may also work with the usual white light, like the common otoscopes.

With the implemented solution, it is possible to get objective digital information of the colour and to processing it in order to perform the diagnostic automatically, thus helping the health professional in its decision.

The concept behind the working principle of the otoscope can be materialized adapting any otoscope of the market, for example the Heine or the Welch Allyn.

BRIEF DESCRIPTION OF THE FIGURES

The following description is based on the attached figures which are presented without any restrictive nature.

DESCRIPTION DETAILED INVENTION

Figure 1:
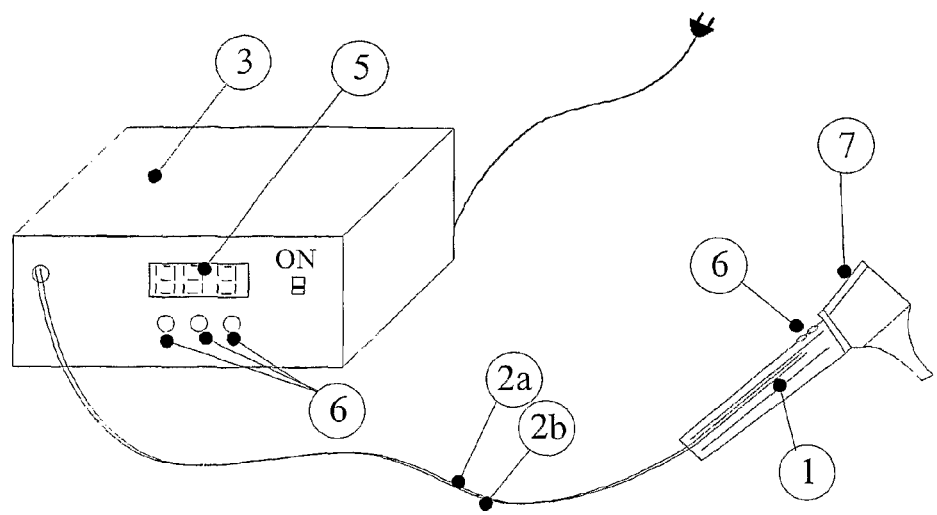
FIG. 1: global digital representation of the otoscope, showing the main parts; the otoscope, the signal conditioning unit and the optical fiber link.
Figure 2:
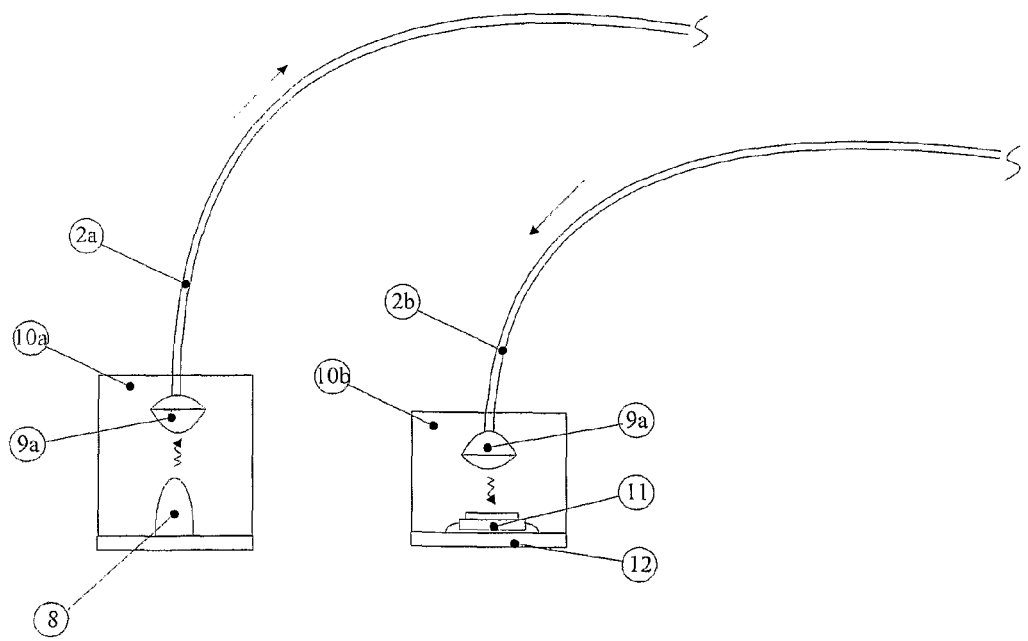
FIG. 2: detail of the light emission and reception solution.

The device object of this invention is essentially characterized by comprise:
- an otoscope (1);
- an electronics unit (3) containing a tri-colour light emitter (8), a tri-colour sensor (11), a digital display (5) and diagnostic signalling LEDs (6);
- optical fibers (2a, 2b) conducting the light generated in the light emitter to the head of the otoscope (1) and conducting also the reflected light in the opposite direction, from the ear to the electronic unit for measuring (3);
- computer means responsible for the acquisition of the light sensor data (11), its processing and storage.

The said device incorporates the ability to emit tri-colour RGB light (8) controlled independently in its three components and to measure the reflected colour also through a RGB sensor.

The otoscope (1) has two buttons (4) for data acquisition control that enable respectively to save or delete the colour sensor read values (11), and has also a magnifying glass (7) to improve the vision of the interior of ear. This lens can be shifted, leaving free access through the speculum. The otoscope allows external connection of a balloon for ear pressurization and depressurization, and this way force the tympanum to move for its elasticity test.

The otoscope (1) is prepared to allow the adaptation of different speculums.

The electronic unit (3) incorporates the control circuits of the light sent to the otoscope and also of the respective reflection conduct by optical fibers (2a, 2b). The intensity and the colour of the light is generated from a set of LEDs (8) controlled by for example, the circuit represented in FIG. 3, which allows the variation of each led current, and thus adjust and vary the intensity of the respective colour (green, red, blue). LEDs (8) are connected to the respective fiber through a special lens (9a), and the entire set is closed by a cover (10a) in order to avoid external interferences.

In the same way the light received by the reflection on the wall of the tympanum is conducted by an optical fiber (2a) up to the RGB sensor (11) through a special lens (9b). The sensor (11) is mounted in a signal conditioning card (12) and the entire set is closed by a cover (10b) in order to prevent interference of environment light. The card (12) output signals are conditioned by a circuit, such as the one depicted in FIG. 4, composed of three inverter amplifiers that isolate the sensor output signals and amplify independently each of the three channels. These amplifiers outputs are added in a summing amplifier whose weights are controlled by the input resistances. The output of the latter corresponds thus to the contribution of the three colour components.

The used colour sensor (11), of a RGB type, allows a high resolution reading, without contact and detects changes in the texture of the surface of skin through the variation of the amount of received light.

The electronic unit (3) has a digital display (5) for displaying the readings and three LEDs (green, yellow and red) to present its diagnosis: green for OK; red for situations of inflammation and yellow for intermediate situations.

The device that was described, produces basically the illumination of the tympanum and the conversion of the reflected colour into an electrical signal to be indicated in a graduated scale and in a light indicator according to the monitored condition.

The said colour sensor (11) can be mounted directly on the otoscope (1) and ear lighting can be done directly by an illumination source, or by optical fibers applied in the otoscope head.

On the other hand, the computer software program allows the analysis of the collected data and has an interface for displaying the results (6).

EXAMPLE OF APPLICATION

Figure 3:
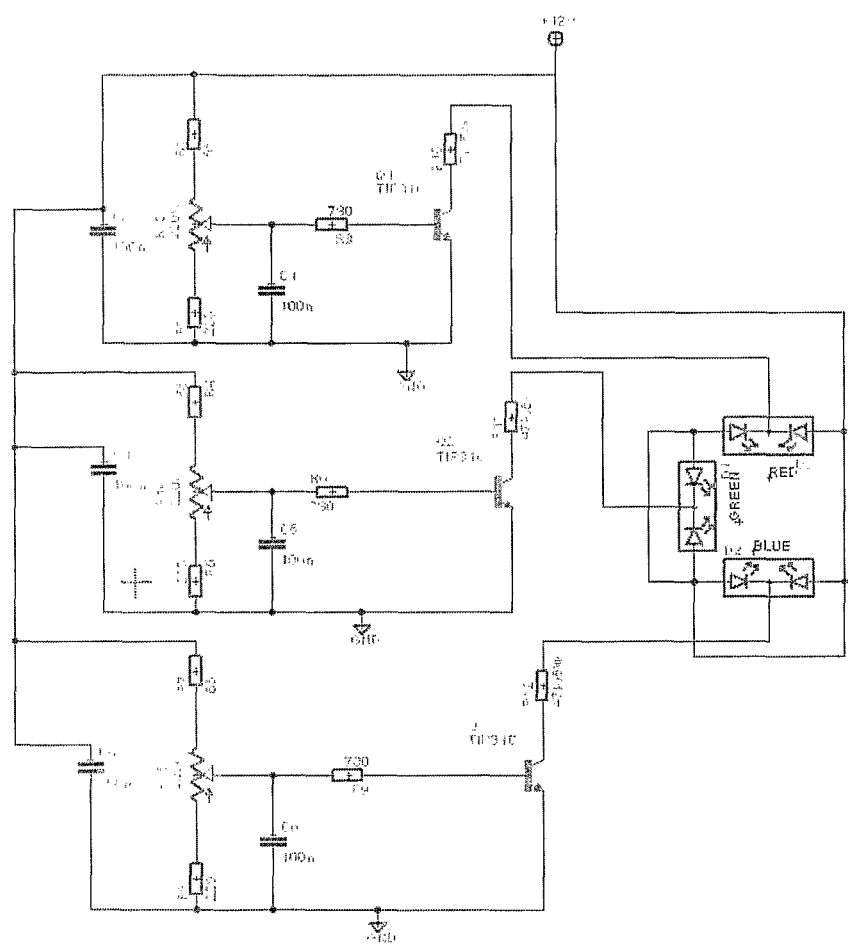
FIG. 3: example of the tri-colour lighting control circuit.
Figure 4:
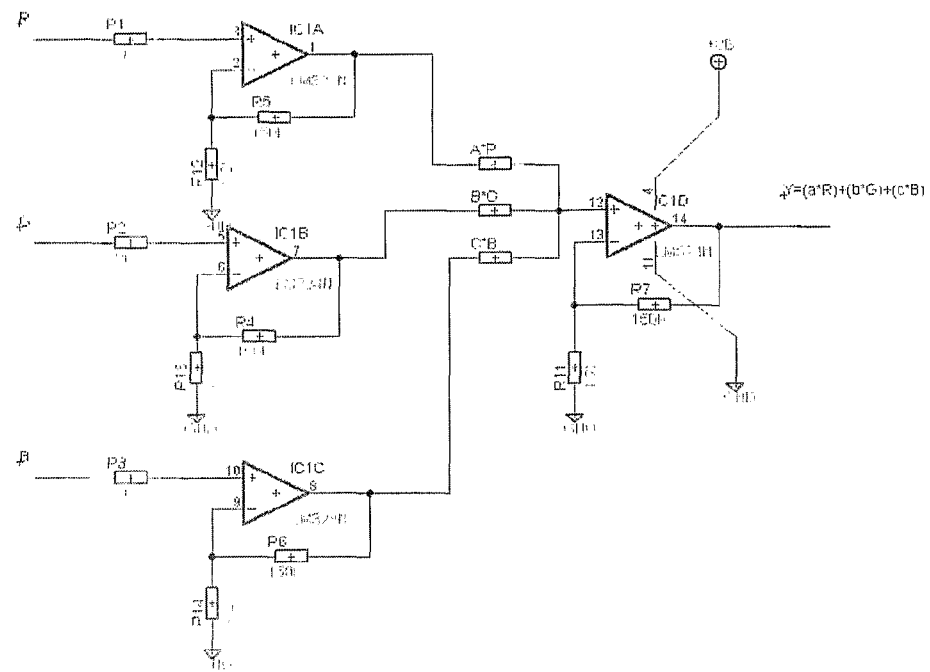
FIG. 4: example of the colour sensor three output signals summing electronic circuit.

In this example, it was used the electronic circuit represented in FIG. 3 to create a light beam composed by three RGB components (red, green, blue) allowing each component strength to be changed by adjusting the corresponding potentiometer. As a tri-colour led, it was used the High Power Three Colour Led from Roithner the Lasertechnik GmbH company. The generated light beam is conducted to the otoscope by an optical fiber, being the connection of the led to the fiber made through a special lens Fibre Coupling Optic, from Roithner Lasertechnik GmbH. In this example, it was used an otoscope from the Heine company, and made two lateral holes for the insertion of the optical fibers. The reflected light is forwarded by the second fiber to the sensor SI S9032-02 photodiode, from Hamamatsu Photonics K.K. In order to facilitate its connection to the rest of the circuit it was used a mainboard Colour Sensor Evaluation Circuit—C9331 also from Hamamatsu. This board includes amplifiers for photo-detectors current conversion into voltage to facilitate its connection to the rest of the circuit. The signs of the three outputs can be analyzed individually or combined in a single output using a circuit as shown in FIG. 4. In this circuit each output is multiplied by a factor defined by the ratio of the resistance of the input amplifiers and its sum made by the amplifier on the right with weights defined by their input resistances. In the case of otitis, its reddish or pink colour, originates in general a higher value in the red component, being also generally more effective the diagnosis lighting in the red range. Thus, in order to reduce costs, the analysis can be done only based on the red colour.

Figure 5:
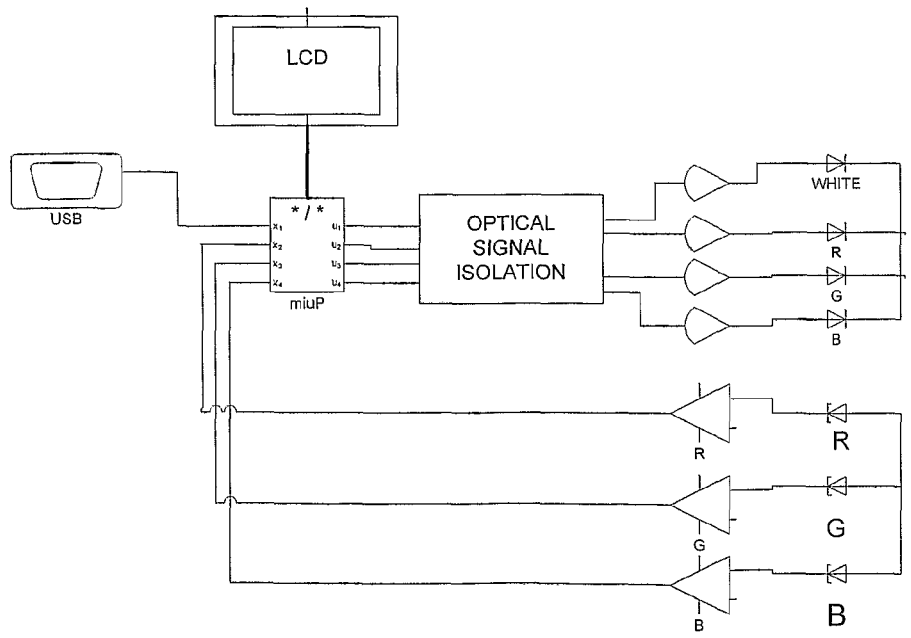
FIG. 5: layout of the electronic circuit controlled by a microcontroller.

A microcontroller from, for example, Microchip as depicted in FIG. 5, simplifies the reading circuit by dismiss all the components of FIG. 3 and allowing the direct link of the conditioning card C9331. Additionally, it is able to record the acquired values, transfer them to a computer through RS232 serial port, or by USB and also show the sensor data and the respective diagnosis in the display. In order to minimize the effects caused by skin colour variation among individuals, it can be used a differential analysis of the two ears, assuming that the second ear is not inflammated.

The schemas are presented as example not limiting in any way and can be subject to modifications and variations carried out by an expert in matter, which, however, fall within the scope of the invention.

LEGEND

1—otoscope;
2a and 2b—optical fiber
3—electronic unit;
4—recording data control buttons;
5—digital display;
6—LEDs diagnostic signalling;
7—lens;
8—tri-colour led;
9a and 9b—lenses for the adaptation of the fiber to the sensor/emitter;
10a and 10b—cover;
11—tri-colour light sensor;
12—electronics signal conditioning card.

BIBLIOGRAPHY

[1] U.S. Pat. No. 5,345,926—Toshio Chikama, Medical Observation Instrument, Tokyo, Japan, 29 Jan. 1993;
[2] WO 03/075761 A2—Richard W. Newman, Combination Otoscope, New York, USA, 7 Mar. 2003;
[3] WO 2007/039843 A2—Vlatko Milosevski et al. Otoscope with Integrated Audio for Patient Listening, Eindhoven, Holanda, 12 Apr. 2007;
[4] US 2005/0171399 A1—Tony C. Rich and Diane B. Rich, TR309-Portable Otoscope Video Viewer, Florida, USA, 18 Jan. 2005;
[5] U.S. Pat. No. 6,093,150—Paul E. Chandler et al., Ultrasound Otoscope, California, USA, 31 Dec. 1997;
[6] U.S. Pat. No. 5,873,819—Craig S. Koch, California, Pneumatic Otoscope, USA, 4 May, 1998;
[7] WO 2005/011484 A1—Ervin Goldfain et al., Otoscope, New York, USA, 26 Jul. 2004.

The invention claimed is:
1. A device for measuring and analyzing the color of the outer ear and ear canal an ear comprising:
   an otoscope;
   an electronic unit containing a tri-color light emitter, a tri-color sensor, a digital display and diagnostic signaling LEDs;
   computer means responsible for the acquisition, processing and storage of light sensor data; optical fibers for conducting light generated in the light emitter in a direc- tion towards a head of the otoscope and for conducting reflected light in an opposite direction, from the ear to the electronic unit for measuring; and means for displaying the results and controlling the equipment, wherein said electronic unit further comprises:
- a tri-color light emitter whose light emission is independently controlled in its three components;
- a tri-color color sensor which saves the values of the three color components; and
- diagnostic signaling LEDs.

2. The device according to claim 1, wherein the device is adapted to be able to use different speculums.

3. The device according to claim 1, wherein the strength and composition of the emitted light is varied.

4. The device according to claim 1, wherein the color sensor is a RGB type color sensor.

5. The device according to claim 1, further comprising a color sensor output measuring with a high resolution, without contact.

6. The device according to claim 1, wherein changes in a texture of a surface of the skin is detected through variations in the amount of received light.

7. The device according to claim 1, wherein the color sensor is mounted directly on the otoscope.

8. The device according to claim 1, wherein ear lighting is made directly by an illumination source or by optical fibers applied in the head of the otoscope.

9. The device according to claim 1, the wherein a software program provides a user interface for displaying results.

10. The device according to claim 1, wherein a software program allows the analysis of collected data.

11. The device according to claim 1, further comprising buttons in the otoscope handler for controlling data acquisition.

* * * * *